United States Patent
Takahashi et al.

(12)

(10) Patent No.: US 6,818,430 B1
(45) Date of Patent: Nov. 16, 2004

(54) PROCESS FOR PRODUCING L-EPI-2-INOSOSE AND NOVEL PROCESS FOR PRODUCING EPI-INOSITOL

(75) Inventors: Atsushi Takahashi, Kawasaki (JP); Kenji Kanbe, Yokohama (JP); Tetsuya Mori, Atsugi (JP); Yuichi Kita, Atsugi (JP); Tsuyoshi Tamamura, Yamato (JP); Tomio Takeuchi, Tokyo (JP)

(73) Assignees: Hokko Chemical Industry Co., Ltd., Tokyo (JP); Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 0 days.

(21) Appl. No.: 09/980,453

(22) PCT Filed: Jun. 7, 1999

(86) PCT No.: PCT/JP00/03687

§ 371 (c)(1),
(2), (4) Date: Feb. 12, 2002

(87) PCT Pub. No.: WO00/75355

PCT Pub. Date: Dec. 14, 2000

(30) Foreign Application Priority Data

Jun. 7, 1999 (JP) .......................................... 11/159861
Nov. 30, 1999 (JP) .......................................... 11/340523
May 23, 2000 (JP) ...................................... 2000-151709

(51) Int. Cl.⁷ ............................ C12P 19/02; C12N 1/20
(52) U.S. Cl. ....................... 435/252.1; 435/72; 435/74; 435/148; 435/155; 435/105
(58) Field of Search ........................... 435/72, 74, 148, 435/105, 155, 252.1

(56) References Cited

PUBLICATIONS

Postemak, Th., Methods in Carbohydrate Chemistry (1962), 1, 289–91.*

Postemak, Theodore, Helv. Chim. Acta (1942), 25, 746–52.*

Kluyver et al., Rec. Trav. Chim., (1939) 58:p. 956–958.*

Anderson et al., Arch Biochem. Biophys., (1958) 78: 518–531.*

* cited by examiner

*Primary Examiner*—Irene Marx
(74) *Attorney, Agent, or Firm*—Stites & Harbison PLLC; B. Aaron Schulman

(57) ABSTRACT

Provided are novel processes for the efficient production of L-epi-2-inosose and epi-inositol which are useful either as various medicines or intermediates for the syntheses of various medicines. In the processes, there is used inexpensive myo-inositol as a starting compound. That is, there is now developed a new process which comprises reacting myo-inositol with a gram-negative bacterium capable of converting myo-inositol into L-epi-2-inosose, and thereby producing L-epi-2-inosose by conversion of myo-inositol into L-epi-2-inosose. Further, a novel process is provided, which comprises reacting the so produced L-epi-2-inosose with a reducing agent made of an alkali metal boron hydride or any other alkali metal hydride in an aqueous reaction medium, to produce epi-inositol and myo-inositol, and then isolating epi-inositol from the resulting reaction product composed of the epi-inositol and myo-inositol.

11 Claims, No Drawings

PROCESS FOR PRODUCING L-EPI-2-INOSOSE AND NOVEL PROCESS FOR PRODUCING EPI-INOSITOL

This application was filed under 35 USC 371 as the national phase of PCT/JP00/03687 filed Jun. 7, 2000.

TECHNICAL FIELD

This invention relates to a one-step process for the production of L-epi-2-inosose which has biological activities in itself and which is also of high value as a starting material for use in the synthesis of medicines and others, wherein a starting compound of inexpensive myo-inositol is used in the process and is converted into L-epi-2-inosose under the action of a microorganism, without involving any chemical synthetic method. This invention further relates to a process for the efficient production of epi-inositol which has biological activities in itself and is useful as a medicine, wherein L-epi-2-inosose is chemically reduced in the process.

BACKGROUND ART

Myo-inositol is a known substance of natural occurrence, which is represented by the following planar structural formula (A)

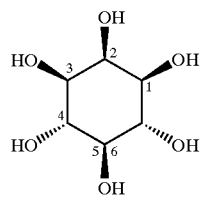

(A)

or by the following steric structural formula (A')

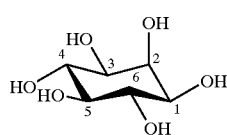

(A')

L-Epi-2-inosose is a known substance represented by the following planar structural formula (B)

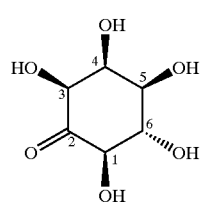

(B)

or by the following steric structural formula (B')

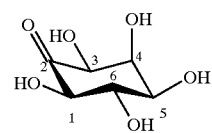

(B')

Further, epi-inositol is a chemically synthesized substance already known, which is represented by the following planar structural formula (C)

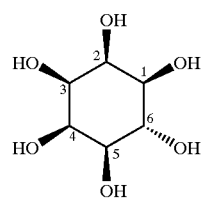

(C)

or by the following steric structural formula (C')

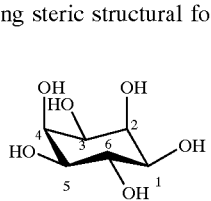

(C')

Epi-inositol is one of the stereo-isomers of myo-inositol.

Inososes (called also as penta-hydroxycyclohexanones or alicyclic ketohexoses) are generally known to have been synthesized by a biological oxidation of inositol [A. J. Kluyver and A. Boezaardt: "Rec. Trav. Chim." 58, p.956 (1939)], by an enzymatic oxidation of inositol [L. Anderson et al.: "Arch. Biochem. Biophys." 78, p.518 (1958)], by oxidation of inositol with air in the presence of a platinum catalyst [K. Heyns and H. Paulsen: "Chem. Ber." 86, p.833 (1953)], or by oxidation of inositol with an oxidizing reagent such as nitric acid [T. Posternak: "Helv. Chim. Acta" 19, p.1333 (1936)].

As such inososes which may be produced by the biological oxidation or enzymatic oxidation of myo-inositol, one of the inositols, there has been known only one inosose, namely scyllo-inosose (called also as myo-inosose-2) [A. J. Kluyver and A. Boezaardt: "Rec. Trav. Chim." 58, p.956 (1939); L. Anderson, et al.,: "Arch. Biochem. Biophys." 78, p.518 (1958)]. There has not been reported any microorganism which is capable of oxidizing myo-inositol into L-epi-2-inosose. L-epi-2-Inosose is useful as the starting material for the synthesis of D-chiro-inositol (abbreviated as DCI) [see U.S. Pat. No. 5,406,005]. DCI is useful as a medicine for the therapy of insulin-resistant diabetes (Published specification of WO90/10439) and is expected to be utilizable as a medicine for ameliorating polycystic ovary syndrome [J. A. Nestler et al.: "NEW Engl. J. Med." 340, p.1314 (1999)]. As a known process for the preparation of L-epi-2-inosose, there is reported (1) a method wherein L-epi-2-inosose is synthesized by oxidizing myo-inositol with nitric acid to form a racemic mixture of DL-epi-2-inosose (that is, (±)-epi-2-inosose), then reducing the resultant racemic mixture with hydrogen in the presence of a platinum oxide catalyst to form epi-inositol, and microbiologically oxidizing the epi-inositol with a microorganism, *Acetobacter suboxydans*, to produce L-epi-2-inosose [T.

Posternak: "Helv. Chim. Acta" 29, p.1991 (1946)]. There is also reported (2) a method wherein L-epi-2-inosose is synthesized as one of such compounds which can be produced by means of an acyloin-condensation of glucodialdose after said glucodialdose had chemically been synthesized from D-glucuronic acid (U.S. Pat. No. 5,406,005).

Inositol is a general name of hexa-hydric alcohols as derived from cyclohexane, and inositol includes nine stereoisomers thereof. There have been found the naturally-occurring inositols which include, five inositols, namely myo-inositol, D-chiro-inositol, L-chiro-inositol, muco-inositol and scyllo-inositol. The other inositols include epi-inositol, allo-inositol, neo-inositol and cis-inositol. These latter four inositols are the non-naturally-occurring inositols, which have been produced by chemical syntheses. Of the non-naturally-occurring inositols, epi-inositol is expected to be utilizable as a medicine for ameliorating mental depression and anxiety syndrome [R. H. Belmaker et al., International Published Specification WO99/22727 of PCT Patent Application, PCT/IL/00523; and R. H. Belmaker et al, "Int. J. Neuro-psychopharmacol." Vol.1, p.31 (1998)].

As the known processes of producing epi-inositol, there are reported (1) a process for synthesis of epi-inositol which comprises oxidizing myo-inositol with nitric acid to form a racemic mixture of D,L-epi-2-inososes, followed by reducing the latter with hydrogen in the presence of a platinum oxide catalyst [T. Posternak: "Helv. Chim. Acta" 29. p.1991 (1946)]; (2) a process for synthesis of epi-inositol which comprises oxidizing a di-hydric alcohol of cyclohexadiene with osmic acid [T. Tschamber et al, "Helv. Chim. Acta" 75, p.1052 (1992)]; (3) a process for synthesis of epi-inositol which comprises hydrogenating tetrahydrobenzoquinone [L. Odier: EP Application published Specification No. 524082]; and (4) a process for synthesis of epi-inositol which comprises protecting muco-inositol appropriately and then subjecting the protected derivative thereof to oxidation and reduction reactions in combination [K. E. Espelia et al, "Carbohydrate Res." 46, p.53 (1976)]. Also, there is known a process for synthesis of epi-inositol which comprises subjecting glucose or galactose to a combination of Ferrier's cyclization reaction with a reducing reaction with a suitable reducing agent [Takahashi et al, "J. Org. Syn. Chem. Soc., Japan" 58, p.120 (2000)].

However, these known processes for the syntheses of L-epi-2-inosose and of epi-inositol are not necessarily satisfactory as such process which may be suited for large-scale production of epi-inositol, because the known processes have such problems that they are complexed to operate, involve environmental pollution and/or are too much expensive. Therefore, there exists keen demands for seeking such a novel process which can produce L-epi-2-inosose in a commercial scale and can operate in a facile way with a high efficiency, as well as such a novel process which can produce epi-inositol in a facile way with a high efficiency. An object of this invention is to provide such a novel process for the production of L-epi-2-inosose and such a process for the production of epi-inositol, which can satisfy the above demands and show many advantages and which can produce either L-epi-2-inosose or epi-inositol efficiently.

DISCLOSURE OF THE INVENTION

We, the present inventors, have eagerly made extensive studies to attain the above-mentioned object of this invention. As a result, we have now found that, when a new microbial strain, Xanthomonas sp. AB10119 strain, which has been isolated from a soil sample by us, is reacted in an aqueous reaction medium with myo-inositol which is available cheaply and has the formula (A) or (A') shown in the above, the 4-hydroxyl group, of myo-inositol can be oxidized (or dehydrogenated) preferentially or substantially preferentially, thereby to produce L-epi-2-inosose of the above formula (B) or (B'). When L-epi-2-inosose so produced is isolated and examined by instrumental analyses such as nuclear magnetic resonance spectroscopic apparatus, mass spectrometric apparatus, polarimetric apparatus and so on, it is confirmed that the L-epi-2-inosose product so obtained is L-epi-2-inosose which has a high optical purity.

Further, we have searched if the microorganisms having an activity or ability to convert myo-inositol into L-epi-2-inosose are present in the natural field extensively. As a result, we have now found and confirmed that some microbial strains having a high activity or ability to oxidize and convert myo-inositol into L-epi-2-inosose exist among taxonomically many varieties of gram-negative bacteria which are belonging to the gram-negative bacteria, for example, gram-negative bacteria of the genus Xanthomonas or the genus Pseudomonas belonging to the family of Pseudomonadaceae; bacteria of the genus Acetobacter or the genus Gluconobacter belonging to the family of Acetobacteraceae; bacteria of the genus Agrobacterium belonging to the family of Rhizobiaceae; bacteria of the genus Erwinia, the genus Enterobacter, the genus Serratia and the genus Yersinia belonging to the family of Enterobacteriacea; and bacteria of the genus Pasteurella or genus Haemophilus belonging to the family of Pasteurellaceae. Of these microbial strains, the above-mentioned Xanthomonas sp. AB 10119 strain may be mentioned particularly as one example of the microbial strains which have a high activity or ability to oxidize and convert myo-inositol into L-epi-2-inosose. There may also be exemplified Pseudomonas sp. AB 10215 strain and Erwinia sp. 10135 strain, which both have been newly isolated by us from soil samples.

Based on these above findings of the present inventors, we have now devised a novel process for the production of L-epi-2-inosose as described below. Thus, we have now found that, when a microorganism, Xanthomonas sp. AB 10119 strain or Pseudomonas sp. AB 10215 strain or Erwinia sp. AB 10135 strain, or other suitable strain is cultivated under aerobic conditions either in a liquid culture medium containing an amount of myo-inositol, usual carbon sources and usual nitrogen sources, or in a liquid culture medium containing an amount of myo-inositol (a portion thereof may serve as a carbon source) and containing nitrogen sources (a portion of the nitrogen sources may serve also as a carbon source, dependently upon the cultivating conditions, if said nitrogen sources as used are the nitrogen sources of the organic nature)but without containing any usual carbon source, it is feasible to produce L-epi-2-inosose efficiently from myo-inositol and to accumulate L-epi-2-inosose in the resulting culture broth. We have further found that, according to the novel process for the production of L-epi-2-inosose as above-mentioned, the L-epi-2-inosose so accumulated in said culture broth can remain dissolved in a culture broth supernatant which is afforded by removing the microbial cells of the microorganism from said culture broth, and that the L-epi-2-inosose can be recovered efficiently as a product of a high purity, by subjecting said culture broth supernatant to a treatment with ion-exchange resins such as cation-exchange resins, anion-exchange resins, etc., or to a treatment with activated carbon, or to a treatment for crystallization of L-epi-2-inosose, or to any combination of these treatments.

Further, we, the present inventors, have made another study, and as a result we have also found that, when the culture broth supernatant is afforded by removing the microbial cells of the microorganism from the aforesaid culture broth which is containing L-epi-2-inosose as produced and accumulated by the cultivation of the micro-organism in the culture medium as mentioned above, and when the resulting culture broth supernatant containing L-epi-2-inosose is then added directly with a suitable amount of a reducing agent such as sodium borohydride or any other reducing agent of the hydride-type equivalent to sodium borohydride and thereafter the L-epi-2-inosose is reacted with the reducing agent, there can be effected the reduction of L-epi-2-inosose into epi-inositol efficiently. In other words, it has been found that L-epi-2-inosose can efficiently be reduced to epi-inositol, by reacting L-epi-2-inosose with said reducing agent within the culture broth supernatant, before this L-epi-inosose has been isolated from the said culture broth supernatant.

We have further carried out various experiments of the procedure for the treatment of myo-inositol with the gram-negative bacteria capable of converting myo-inositol into L-epi-2-inosose by oxidation of myo-inositol, typically the aforesaid Xanthomonas sp. AB 10119 strain, as well as various experiments of the procedure for the direct treatment of L-epi-2-inosose present in the culture broth supernatant with a suitable reducing agent without isolation of the L-epi-2-inosose from said culture broth supernatant so that epi-inositol is produced in said culture broth supernatant. As a result, we have obtained many findings from these experiments. This invention has now been completed on the basis of these findings as obtained by us.

It In a first aspect of this invention, therefore, there is provided a process for the production of L-epi-2-inosose, characterized in that the process comprises reacting myo-inositol with a microorganism capable of converting myo-inositol into L-epi-2-inosose, and thereby converting myo-inositol into L-epi-2-inosose to produce L-epi-2-inosose.

The process for the production of L-epi-2-inosose according to the first aspect of this invention may practically be carried out by one of such two procedures (A) and (B) as described below.

Procedure (A) comprises the steps of cultivating under aerobic conditions a microorganism capable of converting myo-inositol into L-epi-2-inosose, in a liquid culture medium containing an amount of myo-inositol, carbon sources and nitrogen sources, thereby to react said microorganism with myo-inositol and to produce and accumulate L-epi-2-inosose in the resulting culture broth, and then harvesting said culture broth; as well as the steps of removing the microbial cells of said microorganism from the resulting culture broth, thereby to afford a culture broth supernatant containing the L-epi-2-inosose so produced and accumulated therein, and then recovering L-epi-2-inosose from the resulting culture broth supernatant by subjecting said culture broth supernatant to a treatment with ion-exchange resin(s), or to a treatment with activated carbon, or to a treatment for crystallization of L-epi-2-inosose, or to a combination of these treatments.

Procedure (B) comprises the steps of cultivating the microorganism capable of converting myo-inositol into L-epi-2-inosose, in a liquid culture medium and then separating the microbial cells of said microorganism from the resulting culture broth; the steps of adding the so separated microbial cells to a buffer solution or a liquid culture medium containing an amount of myo-inositol dissolved therein, and reacting the so added microbial cells with myo-inositol in said buffer solution or said liquid culture medium, to convert myo-inositol into L-epi-2-inosose in the resulting reaction solution or in the resulting culture broth; and the step of recovering the L-epi-2-inosose so produced and accumulated in said reaction solution or said culture broth, by subjecting said reaction solution or culture broth to a treatment with ion-exchange resin (s), or to a treatment with activated carbon, or to a treatment for crystallization of L-epi-2-inosose, or to any combination of these treatments.

The microorganism to be used in the process according to the first aspect of this invention may be any strain of microorganisms, so long as it possesses such an activity or ability that said strain is capable of converting myo-inositol into L-epi-2-inosose.

As exemplified concretely, there are a variety of bacteria which can produce L-epi-2-inosose from myo-inositol, as described hereinbefore. For example, there are the AB 10119 strain, AB 10215 strain and AB 10135 strain which we have isolated from soil samples as explained above, and which are the most effective strains of the bacteria to be used in the process of this invention. Microbiological properties of said three bacterial strains are shown in Table 1a, Table 1b, Table 1c and Table 1d, hereinafter.

By the way, we have carried out our experiments for the identification of said three bacterial strains in accordance with the following Japanese text books titled as Shin Saikin Baichigaku Koza (2nd Edition, published by Kindai Shuppan); A Guide on Identification of Medical Bacteria (2nd Edition, published by Kindai Shuppan); and A Manual on Practice of Bacteriology (published by Maruzen Publishing Company). Further, the results of our experiments as above were evaluated with reference to Bergey's Manual of Systematic Bacteriology Vol.1 (1984) to identify the bacterial strains as isolated.

TABLE 1a-1

| Morphological properties | AB 10119 strain | AB 10215 strain | AB 10135 strain |
|---|---|---|---|
| (1) Shape of cells: | Rods of 0.4–0.6 × 0.6–4.0 μm in size, with pleomorphic. | Rods of 0.3–0.5 × 0.6–6.5 μm in size, with pleomorphic. | Rods of 0.4–0.6 × 0.8–2.0 μm in size, without pleomorphic. |
| (2) Mobility: | — | — | — |
| (3) Growth characteristics on nutrient agar plate: | Growth is moderate, form of colony is a round shape, the surface is smooth and glossy, ochreous to yellow in color. | Growth is abundant, form of colony is a round shape, the surface is smooth and glossy, ochreous in color. | Growth is very slight, form of colony is a round shape, the surface is smooth and glossy, milkwhite in color. |
| (4) Growth characteristics on the minimum culture medium (comprising a carbon source of glucose): | Growth is slight. | Growth is abundant. | No growth is observed. |

TABLE 1a-2

| physiological and biochemical properties: | AB 10119 strain | AB 10215 strain | AB 10135 strain |
|---|---|---|---|
| (1) Gram's staining: | − | − | − |
| (2) OF test: | O (Oxidative) | O (Oxidative) | F (Fermentative) |

TABLE 1a-2-continued

| physiological and biochemical properties: | AB 10119 strain | AB 10215 strain | AB 10135 strain |
|---|---|---|---|
| (3) Growth under aerobic conditions: | + | + | + |
| (4) Growth under anaerobic conditions: | − | − | +(weak) |
| (5) Growth temperature: | | | |
| 8° C. | − | − | − |
| 10° C. | − | − | + |
| 13° C. | + | + | + |
| 17° C. | + | + | + |
| 21° C. | + | + | + |
| 37° C. | + | + | + |
| 40° C. | + | + | − |
| 42° C. | − | − | − |
| 47° C. | − | − | − |
| (6) Salt tolerance: | | | |
| 0% | + | + | + |
| 2% | + | + | + |
| 5% | − | − | + |
| 10% | − | − | − |

TABLE 1b

| physiological and biochemical properties: | AB 10119 strain | AB 10215 strain | AB 10135 strain |
|---|---|---|---|
| (7) Growth pH: | | | |
| pH 3 | − | − | − |
| pH 4 | − | − | + |
| pH 5 | + | + | + |
| pH 6 | + | + | + |
| pH 7 | + | + | + |
| pH 8 | + | + | + |
| pH 9 | +(weak) | +(weak) | + |
| pH 10 | − | − | +(weak) |
| (8) Formation of pigment: | | | |
| Mannit-Yeast extract-Agar medium (for detecting water-insoluble pigment): | Microbial cells were pigmented with light ochreous to yellow. | Microbial cells were slightly pigmented with yellow color. | − |
| King's medium (for detecting water-soluble pigment): | Formation of light yellow pigment in agar. | Formation of light yellow pigment in agar. | − |
| (9) Formation of cytochrome oxidase: | − | − | − |
| (10) Formation of catalase: | + | + | + |
| (11) Reduction of nitrate: | − | + | + |
| (12) Formation of hydrogen sulfide: | − | − | − |
| (13) Formation of acetoin: | + | − | + |
| (14) Liquefaction of gelatin: | + | + | + |
| (15) Decomposition of Tween 80: | + | + | − |
| (16) Formation of indole: | − | − | − |
| (17) Utilization of malonic acid: | − | − | − |
| (18) Decomposition of ONPG: | + | + | + |
| (19) Decomposition of esculin: | + | + | − |

TABLE 1c

| physiological and biochemical properties: | AB 10119 strain | AB 10215 strain | AB 10135 strain |
|---|---|---|---|
| (20) Deoxyribonuclease activity: | + | + | − |
| (21) Utilization of citric acid: | + | + | − |
| (22) Decarboxylase activity on amino acids: | | | |
| L-lysine | − | − | − |
| L-arginine | − | − | − |
| L-ornithine | − | − | − |
| (23) Decomposition of urea: | − | − | − |
| (24) Decomposition of acetamide: | − | − | − |
| (25) Litmus milk: | Not coagulated | Not coagulated | Not coagulated |
| (26) Decomposition of starch: | − | − | − |
| (27) Sensitivity test on pigments and chemicals: | | | |
| 0.01% methyl green | + | + | − |
| 0.01% thionine | + | + | − |
| 0.01% lead acetate | − | − | − |
| (28) Formation of acid from various sugars: | | | |
| Glucose | + | + | + |
| Xylose | + | + | + |
| Mannose | + | + | + |
| Arabinose | + | + | + |
| Fructose | + | + | + |
| Maltose | + | + | + |
| Rhamnose | − | − | − |
| Mannitol | − | − | + |
| Sucrose | − | − | + |
| Adonitol | − | − | − |
| Myo-inositol | − | − | − |

TABLE 1d

| physiological and biochemical properties: | AB 10119 strain | AB 10215 strain | AB 10135 strain |
|---|---|---|---|
| (28) Formation of acid from various sugars: | | | |
| Sorbitol | − | − | − |
| Galactose | + | + | + |
| Trehalose | − | − | − |
| Cellobiose | + | + | + |
| Inulin | − | − | − |
| Dulcitol | − | − | − |
| Salicin | + | − | − |
| Lactose | − | + | + |
| Glycerol | − | − | + |
| Raffinose | − | + | − |
| a-Methyl-glucose | − | − | − |
| (29) Utilization of carbon source: | | | |
| Glucose | + | + | − |
| Cellobiose | + | + | − |
| Maltose | + | + | − |
| Lactose | + | + | − |
| Trehalose | + | + | − |
| Galactose | + | + | − |
| D-fructose | + | + | − |
| Myo-inositol | − | + | − |
| Salicin | − | + | − |
| L-histidine | + | + | − |
| L-glutamic acid | + | + | − |
| Glycine | − | − | − |
| Pantothenic acid | − | + | − |
| Asparagine | − | +(weak) | − |
| Methionine | − | + | − |

TABLE 1d-continued

| physiological and biochemical properties: | AB 10119 strain | AB 10215 strain | AB 10135 strain |
|---|---|---|---|
| (30) Type of Ubiquinone molecules: | Q8 | Q8 | Q8 |
| (31) GC content of DNA (by HPLC method) | 68 | 68 | 50 |

The morphological properties of the abovementioned AB 10119 strain are mainly characterized by that this strain is gram-negative rods which forms colonies as pigmented with yellow color and has 0.4–0.6×0.6–4.0 μm in size. This AB 10119 strain is catalase-positive and oxidase-negative and decomposes glucose under aerobic conditions to produce acid. The growth of this AB 10119 strain in a minimal medium is poor, but the addition of methionine to the minimal medium gives a good growth of this strain. This AB 10119 strain has no ability to reduce nitrates and is susceptible to 0.01% of methyl green and thionine. The type of the ubiquinone molecule in the cells of the AB 10119 strain is QB and the GC contents of the DNA are 68%.

Summarizing these morphological properties of AB 10119 strain, this strain has been judged to be a microbial strain which belongs to the genus Xanthomonas. According to Bergey's Manual of Systematic Bacteriology Vol.1, pp.119–210 (1984), the known bacteria of the genus Xanthomonas include five species, namely *Xanthomonas campestris; Xanthomonas fragariae; Xanthomonas albilineans; Xanthomonas axonopodis*; and *Xanthomonas ampelina*.

As a result of our examination of the morphological properties of AB 10119 strain in comparison with those of the above-mentioned known five species, the AB 10119 strain appears to be most resemble to a known species, *Xanthomonas campestris*. Since, however, the morphological properties of this AB 10119 strain are not coincident completely with those of *Xanthomonas campestris*, we have designated this new strain as Xanthomonas sp. AB 10119 strain to distinguish it from said known species and we have deposited it in the authorized Japanese depository, the National Institute of Bioscience and Human Technology, Agency of Industrial Science and Technology, located at 1-3, 1-chome, Higashi, Tsukuba-City, Ibaraki Prefecture, Japan, under a deposit number of FERM P-17382 (Deposit date: May 7, 1999). Then, this AB 10119 strain has been re-deposited under a deposit number of FERM BP-7168 in terms of Budapest Treaty in the same National Institute since May 23, 2000.

The morphological properties of the abovementioned AB 10215 strain are mainly characterized by that this strain is gram-negative rods which form colonies as pigmented with pale yellow color and has 0.3–0.5×0.6–6.5 μm in size. This AB 10215 strain is catalase-positive and oxidase-negative and decomposes glucose under aerobic conditions to produce acid. The growth of this AB 10215 strain in a minimal medium is good and has an ability to reduce nitrates and is susceptible to 0.01% of methyl green and thionine. The type of the ubiquinone-molecule in the cells of the AB 10215 strain is Q8 and the GC contents of DNA are 68%.

Summarizing these morphological properties of the AB 10215 strain, this strain appears to be most resemble to a known strain, *Pseudomonas maltophilia*, described in Bergey's Manual of Systematic Bacteriology Vol.1, pp.140–199 (1984). However, the AB 10215 strain are not coincident completely with a known species, *Pseudomonas maltophilia*, so that we have designated this new strain as Pseudomonas sp. AB 10215 to distinguish it from the said known species, and we have deposited it in the Japanese depository, The National Institute of Bioscience and Human Technology, Agency of Industrial Science and Technology, located at 1-3, 1-chome, Higashi, Tsukuba-City, Ibaraki Prefecture, Japan, under a deposit number of FERM P-17804 (Deposit date: Mar. 31, 2000). Then, this AB 10215 strain has been re-deposited under FERM BP-7170 in terms of Budapest Treaty in the same National Institute since May 23, 2000.

The morphological properties of the abovementioned AB 10135 strain are mainly characterized by that this strain is gram-negative rods which forms colonies as pigmented with milk white color and has 0.4–0.6×0.8–2.0 μm in size. This AB 10135 strain can decompose glucose both under the aerobic conditions and anaerobic conditions, but the growth of the AB 10135 strain is very much poorer under the anaerobic conditions, as compared with its growth under the aerobic conditions. Further, this AB 10135 strain is catalase-positive and oxidase-negative, and decomposes glucose under aerobic conditions to produce acid. The growth of this AB 10315 strain in an ordinary nutrient agar medium is very slight, but the addition of 5% sucrose to the nutrient agar medium can give a very abundant growth of this strain. The type of the ubiquinone molecule in the cells of the cells of this strain is Q8, and the GC contents of DNA are 68%

Summarizing these morphological properties of the AB 10135 strain, this strain has been judged to belong to the genus Erwinia. According to Bergey's Manual of Systematic Bacteriology Vol.1, pp.469–476 (1984), the known bacterial strain belonging to the genus Erwinia have been classified into 15 species, but the AB 10135 strain are not coincident completely with any of the known strains. Thus, we have designated this new AB 10135 strain as Erwinia sp. AB 10135 to distinguish it from the known Erwinia strains, and we have deposited it in the Japanese depository, the National Institute of Bioscience and Human Technology, Agency of Industrial Science and Technology, located at 1-3, 1-chome, Higashi, Tsukuba-City, Ibaraki Prefecture, Japan, under a deposit number of FERM P-17803 (Deposit date: Mar. 31, 2000). Then, this AB 10315 strain has been re-deposited under a deposit number of FERM BP-7169 in terms of Budapest Treaty in the same National Institute since May 23, 2000.

Now, the two procedures (A) and (B) according to the first aspect of this invention above-mentioned are described in more details.

In the procedure (A), there is carried out a first step wherein the microorganism capable of converting myo-inositol into L-epi-2-inosose is cultivated under aerobic conditions in a nutrient liquid culture medium containing an amount of myo-inositol, carbon sources and nitrogen sources, thereby to produce and accumulate L-epi-2-inosose in the resulting culture broth.

The composition of the liquid culture medium to be used in said first step of the process is not specifically limited, so long as it can achieve the purpose intended. The liquid culture medium as used may be any culture medium which contains an amount of myo-inositol as the starting material to be converted into L-epi-2-inosose, and which, in addition, contains carbon sources, nitrogen sources, nutrient sources of organic nature, inorganic salts, and others. Either of the known synthetic culture medium and the known natural culture medium may be used. It is desirable that the liquid culture medium to be used here contains 0.1% to 40%, preferably 20% to 30% of myo-inositol, contains as the carbon source, 0.1% to 20%, preferably 0.5% to 5% of glucose, sucrose, maltose or starch, and contains as the nitrogen source, 0.01% to 5.0%, preferably 0.5% to 2.0% of yeast extract, peptone, casamino acids, ammonium sulfate, ammonium chloride, ammonium nitrate or urea, and so on. Further, it is advantageous that the liquid culture medium is added with inorganic salts capable of producing ions of sodium, potassium, calcium, magnesium, cobalt, manganese, zinc, iron, copper, molybdenum, phosphate, sulfate or others, if necessary. L-epi-2-Inosose can be produced efficiently, when the cultivation of the microorganism used is carried out while the concentration of hydrogen ion in the resulting culture broth is adjusted to a pH value of 4 to 10, preferably of 50 to 9.

The conditions for cultivation of the microorganism may vary dependently upon the nature of the strain of microorganism and the culture medium as used, but the cultivation temperature may be at a temperature of 5 to 40° C., preferably 20 to 37° C. It is also preferred that the cultivation of the microorganism is carried out under aerobic conditions by shaking the liquid culture medium or by blowing air into the liquid culture medium, and so on. The cultivation period may be such period of time for which the myo-inositol present in the resulting culture broth has completely consumed and the amount of L-epi-2-inosose so produced and accumulated in the resulting culture broth has become a maximum. The cultivation period may usually be 1 to 14 days, preferably 3 to 10 days. Thus, the culture broth containing L-epi-2-inosose may be afforded in the first step of the process mentioned above.

Then, there is carried out a second step wherein the desired L-epi-2-inosose is recovered from the culture broth. For the purpose of this recovery, one can apply a usual process or processes which may conventionally be used for the isolation and purification of any usual water-soluble and neutral substances from the culture broth. Thus, the microbial cells of the microorganism used in this invention are first removed from the resultant culture broth containing L-epi-2-inosose, and then the resulting culture broth supernatant is treated with activated carbon or with ion-exchange resin(s), so that all of the impurities, except L-epi-2-inosose, can be removed almost from the culture broth supernatant. For the purpose of effecting the treatments with ion-exchange resins, however, it is impossible to use a strongly basic anion-exchange resins of $OH^-$ form, because the latter resins can decompose L-epi-2-inosose chemically. After this, L-epi-2-inosose as desired can be isolated from the culture broth supernatant which has been so treated with the activated carbon or ion-exchange resins, when said culture broth supernatant is treated in such way that L-epi-2-inosose is crystallizated from the solution and, if necessary, is further recrystallizated.

For the purpose of effecting the recovery of L-epi-2-inosose from said culture broth supernatant, more concretely, it is preferred to take such procedure which comprises passing the culture broth supernatant containing the accumulated L-epi-2-inosose through a column of a strongly acidic cation-exchange resin, for example, Duolite (Registered Trade Mark) C-20 ($H^+$ form) to remove undesirable components, collecting the effluent liquid from the column, passing a volume of deionized water through this column for washing the column, collecting the resultant aqueous washings, combining said effluent liquid with the aqueous washings, passing the resultant combined solution through a column of a weakly basic anion-exchange resin, for example, Duolite (Registered Trade Mark) A368S (in the free base form), collecting the resulting effluent liquid from the latter column, passing a volume of deionized water through the latter column for washing the column, collecting the resultant aqueous washings, and combining the latter effluent liquid with the latter aqueous washings, so as to afford an aqueous solution which contains L-epi-2-inosose but does not contain substantially any impurities. The aqueous solution so afforded may then be concentrated to give a concentrated solution of L-epi-2-inosose, which is then added with a suitable amount of ethanol. When the resulting mixture containing L-epi-2-inosose and ethanol is allowed to stand at room temperature or lower temperature overnight, L-epi-2-inosose can be crystallized in the form of pure crystals.

In the aforesaid procedure (B) of the process according to the first aspect of this invention, there are carried out the several steps which comprise cultivating a microorganism having the required capability, in a culture medium, separating the microbial cells of said microorganism from the resulting culture broth, and adding the so separated microbial cells to a buffer solution or a liquid culture medium containing myo-inositol, and then reacting the microbial cells with myo-inositol in said buffer solution or said liquid culture medium, to produce L-epi-2-inosose in the resulting reaction solution which is afforded from said buffer solution or said liquid culture medium.

As the microbial cells to be used in the step of reacting myo-inositol with the microbial cells, there may be used either the cells which have been collected by separating the cells from the culture broth as obtained in the first step of Procedure (A), or the cells which have been harvested by cultivating said microorganism in a separate step under suitable cultivation conditions. The collection of the microbial cells from the culture broth may be effected in a known manner for the separation of microbial cells by subjecting the culture broth to centrifugation, filtration or similar method.

As the reaction medium to be used for the reaction of myo-inositol with the microbial cells, either a liquid culture medium or a buffer solution may be used. As said liquid culture medium, there may be used a culture medium having a similar composition to that of the culture medium which is used in the aforesaid first step of Procedure (A). There may also be used such a liquid medium, which is composed of such supernatant of a culture broth that may have been obtained by cultivating said microorganism in a separate step, followed by removing the microbial cells of the microorganism from the resulting culture broth. As said buffer solution, there may be used a phosphate buffer solution, Tris buffer solution, or Good's CHES buffer solution, and other, at a concentration of 10 to 500 mM, preferably 20 to 100 mM. The initial concentration of myo-inositol in a solution of myo-inositol as dissolved in a buffer solution or in a liquid culture medium may preferably be at a level of 0.1 to 40% (by weight).

The reaction conditions for effecting the reaction of myo-inositol with the microbial cells may vary depending upon the nature of the microbial strain and the culture medium or the buffer solution which are employed. Usually, the reaction temperature may be at 5 to 60° C., preferably 10 to 45° C., and the reaction time may be 1 to 50 hours, preferably 3 to 48 hours. The pH of the liquid culture medium or the buffer solution may be at 2 to 10, preferably 3 to 9.

After the completion of the reaction of myo-inositol with the microbial cells, the isolation of the intended product, L-epi-2-inosose, from the resulting reaction solution may be effected in the same manner as that used in the aforesaid second step of Procedure (A).

According to a second aspect of this invention, there is provided a process for the production of epi-inositol, characterized in that the process comprises the steps of reacting a microorganism capable of converting myo-inositol into L-epi-2-inosose, with myo-inositol in an aqueous reaction medium to produce L-epi-2-inosose in said aqueous reaction medium, thereby affording the resulting reaction solution containing the microbial cells of said microorganism and the produced L-epi-2-inosose therein, removing the microbial cells from said reaction solution to give a reaction solution filtrate containing L-epi-2-inosose, adding an appropriate reducing agent directly to said reaction solution filtrate containing L-epi-2-inosose, and reacting the reducing agent with L-epi-2-inosose to produce epi-inostol and myo-inositol.

This process according to the second aspect of this invention may be carried out in practice by one of the following three Procedures (C), (D) and (E).

Procedure (C) of the process according to the second aspect of this invention comprises the step (first stage) of cultivating under aerobic conditions a microorganism capable of converting reaction myo-inositol into L-epi-2-inosose in such an aqueous medium composed of a liquid culture medium containing an amount of myo-inositol, carbon sources and nitrogen sources, in the same manner as that of the step for cultivation of the microorganism described in Procedure (A) of the process of the first aspect of this invention, so that the myo-inositol is reacted with said microorganism in the aqueous reaction medium or in the resulting culture broth, thereby to convert the myo-inositol into L-epi-2-inosose and thus to produce and accumulate L-epi-2-inosose in said culture broth, and so that there is thus afforded the culture broth which is namely the resulting reaction solution containing the microbial cells of said microorganism and L-epi-2-inosose; as well as the step (second stage) of removing the microbial cells of said microorganism from the so afforded resulting culture broth, namely said resulting reaction solution, thereby to produce a culture broth supernatant, namely the filtrate of the reaction solution containing the produced L-epi-2-inosose, without effecting any isolation of L-epi-2-inosose; and the steps (third stage) of adding directly to the resultant culture broth supernatant (namely, said reaction solution filtrate) an alkali metal boron hydride, an alkali metal tri-alkoxyboron hydride or an alkali metal boron cyanide as a reducing agent, and effecting the reductive reaction of L-epi-2-inosose with this reducing agent, thereby to produce epi-inositol and myo-inositol in said culture broth supernatant, namely said reaction solution filtrate; the step (fourth stage) of recovering the epi-inositol and myo-inositol from the resulting reaction solution of the reductive reaction which is namely the culture broth supernatant containing epi-inositol and myo-inositol so produced; and the step (fifth stage) of separating the so recovered epi-inositol and myo-inositol from each other.

Procedure (D) of the process of the second aspect of this invention comprises the steps (first stage) of cultivating under aerobic conditions a microorganism capable of converting myo-inositol into L-epi-2-inosose in a liquid culture medium containing carbon sources and nitrogen sources, in the same manner as that of the step for cultivation of the microorganism described in Procedure (B) of the process of the first aspect of this invention, thereby to afford a culture broth of said microorganism, and then separating the microbial cells of said microorganism from the resultant culture broth; the step (second stage) of reacting the so separated microbial cells of the said microorganism with myo-inositol in an aqueous reaction medium composed of an aqueous buffer solution or a liquid culture medium, to produce L-epi-2-inosose, in said aqueous reaction medium; the step (third stage) of removing the microbial cells of said microorganism from the resulting aqueous reaction solution containing the microbial cells of said microorganism and the so produced L-epi-2-inosose therein, to afford a resulting filtrate of the reaction solution from which the microbial cells have been removed but in which L-epi-2-inosose remains dissolved; the steps (fourth stage) of adding to the reaction solution filtrate an alkali metal boron hydride, an alkali metal tri-alkoxyboron hydride or an alkali metal boron cyanide as a reducing agent, and effecting the reductive reaction of L-epi-2-inosose with said reducing agent, thereby to produce epi-inositol and myo-inositol in said reaction solution filtrate; the step (fifth stage) of recovering the epi-inositol and myo-inositol from the resulting reaction solution of the reductive reaction which is containing the epi-inositol and myo-inositol so produced; and the step (sixth stage) of separating the so recovered epi-inositol and myo-inositol from each other.

Procedure (E) of the process of the second aspect of this invention is modified from the above Procedures (C) and (D). Procedures (E) comprises such a process wherein, before conducting the step of the reductive reaction of L-epi-2-inosose with the reducing agent as added, there is conducted such a preliminary step in which the pH of the aqueous medium composed of the culture broth supernatant or the reaction solution filtrate containing L-epi-2-inosose therein is once adjusted to an alkaline pH in a range of pH 8 to 12; and wherein there is then conducted the step which comprises adding to the alkaline aqueous medium containing L-epi-2-inosose and having a pH of 8 to 12, an alkali metal boron hydride, an alkali metal tri-alkoxyboron hydride or an alkali metal boron cyanide as the reducing agent, and effecting the reductive reaction of L-epi-2-inosose with said reducing agent. According to Procedure (E), the desired epi-inositol can be produced in such way that the yield of epi-inositol as produced is much greater than that of the by-produced myo-inositol.

The microorganisms to be used in the process according to the second aspect of this invention may be the same as those which are used in the process according to the first aspect of this invention, and which are capable of converting myo-inositol into L-epi-2-inosose.

The above-mentioned Procedures (C) and (E) of the process according to the second aspect of this invention are now explained in more details.

In Procedure (C) of the process according to the second aspect of this invention, in a brief, there are conducted a first stage comprising inoculating a nutrient liquid culture medium containing an amount of myo-inositol, with a microorganism having the desired capability, cultivating the inoculated microorganism under aerobic conditions, thereby to convert myo-inositol and to produce and accumulate L-epi-2-inosose in the resultant culture broth, and harvesting the culture broth containing L-epi-2-inosose desired; and a second stage comprising of removing the microbial cells from the harvested culture broth to afford a culture broth supernatant containing L-epi-2-inosose; a third stage comprising adding to said culture broth supernatant directly a suitable reducing agent without effecting any isolation of L-epi-2-inosose from the culture broth supernatant, and then effecting the reductive reaction of L-epi-2-inosose; and a fourth stage comprising recovering the so produced epi-inositol from the resulting reaction solution.

Thus, Procedure (C) of the process of the second aspect of this invention is started by conducting the first stage which comprises cultivating a microorganism having the desired capability in a liquid culture medium containing an amount of myo-inositol, thereby to convert myo-inositol and to produce and accumulate L-epi-2-inosose in the resulting culture broth, and harvesting the culture broth containing L-epi-2-inositol. This first stage may be carried out in the entirely same manner as that for the first step of the aforesaid Procedure (A).

In the second stage of Procedure (C), there is then effected the step of removing the microbial cells of the microorganism from the culture broth as harvested in said first stage, to afford the culture broth supernatant containing L-epi-2-inosose. In the subsequent, third stage, the reductive reaction of L-epi-2-inosose is carried out after a hydride has been added as the reducing agent directly to the resulting culture broth supernatant, so that epi-inositol and myo-inositol can be produced in said culture broth supernatant. The reducing agent used may be those which are capable of reducing L-epi-2-inosose to epi-inositol in an aqueous medium. The reducing agent may desirably be, for example, sodium boron hydride, lithium boron hydride, potassium boron hydride, sodium trimethoxyboron hydride or sodium boron cyanide hydride. The reductive reaction may be effected at a temperature of 0° C. to room temperature. The reductive reaction is finished at a time point when L-epi-2-inosose has been consumed completely, or at a time point when the amount of the desired reaction products has reached an appropriate level intended. Thus, in this third stage, there is afforded the culture broth supernatant containing the produced epi-inositol and myo-inositol, as the reaction solution of the reduction reaction.

Then, there is conducted the fourth stage where epi-inositol and myo-inositol as produced are recovered from the culture broth supernatant which was obtained as the reaction solution of the reduction reaction in the third stage. In this fourth stage for the recovery, it is preferred to follow such a method which comprises passing said culture broth supernatant containing epi-inositol and myo-inositol as obtained from said third stage, through a column of a strongly acidic cation-exchange resin, for example, Duolite (Registered Trade Mark) C-20 (H$^+$ form), for the purpose of the removal of undesirable components, then collecting the effluent liquid from the column, washing the column of cation-exchange resin with a volume of deionized water by passing the water through this column, collecting the resultant aqueous washings, combining the so collected effluent liquid with the aqueous washings, passing the so combined solution through a column of a strongly basic anion-exchange resin, for example, Duolite (Registered Trade Mark) A113 (OH$^-$form), collecting the effluent liquid from the latter column, washing the column of the anion-exchange resin with a volume of deionized water by passing the water through the latter column, collecting the resultant aqueous washings, and combining the so collected effluent liquid with the latter aqueous washings, thereby to afford a resulting aqueous solution which contains epi-inositol and myo-inositol but is substantially free from the impurities.

In the final (the fifth) stage of the Procedure (C), epi-inositol and myo-inositol each are isolated separately from the aqueous solution of epi-inositol and myo-inositol which was afforded in the fourth stage above. For the purpose of isolating these products, it is preferred to take such a procedure which comprises concentrating said aqueous solution of epi-inositol and myo-inositol under a reduced pressure, passing the resultant concentrate through a column of a strongly basic anion-exchange resin, for example, Amberlite (Registered Trade Mark) CG-400 (OH–form), then eluting the column of the anion-exchange resin with a volume of deionized water by passing the water through this column, collecting separately the eluate fraction(s) containing a main portion of myo-inositol, and the eluate fraction(s) containing the desired epi-inositol, as the separate fractions. The aqueous solution (the eluate fractions) containing epi-inositol may be concentrated, and to the resulting concentrated solution of epi-inositol is added an appropriate amount of ethanol. The resulting mixture is allowed to stand at room temperature or lower temperature overnight so that a pure product of epi-inositol can be crystallized in the form of crystals.

In addition, in respect of Procedure (C), if the fourth stage of Procedure (C) is conducted in such a manner that the culture broth supernatant containing epi-inositol as produced from the reductive reaction is treated with plural columns of ion-exchange resins which are arranged in series, there can be obtained such an aqueous solution which contains epi-inositol and myo-inositol but is substantially free from the impurities. According to our findings, it has been found that epi-inositol can be isolated efficiently from myo-inositol, if the fifth stage of Procedure (C) is conducted by a method which comprises concentrating the above-mentioned aqueous solution containing epi-inositol and myo-inositol but being free from the impurities; passing the resulting concentrated solution through a column of a strongly acidic cation-exchange resin comprising certain styrene-polymer having sulfonic acid group as the ion-exchange group (Ca$^{2+}$ form), for example, Diaion (Registered Trade Mark) UBK 520M (Ca$^{2+}$ form); thereby adsorbing epi-inositol and myo-inositol in said column; and then eluting this column with a volume of deionized water.

In Procedure (D) of the process of the second aspect of this invention, in a brief, there are conducted a first stage comprising cultivating a microorganism having the desired capability in a nutrient liquid culture medium under aerobic conditions, and separating the microbial cells of the microorganism from the resulting culture broth, thereby to obtain a large amount of said microbial cells; a second stage comprising reacting the so separated microbial cells with myo-inositol in an aqueous reaction medium composed of either a buffer solution or a liquid culture medium containing an amount of myo-inositol dissolved therein, thereby to produce L-epi-2-inosose in said aqueous reaction medium; a third stage comprising removing the microbial cells from the resulting reaction solution, to afford the reaction solution filtrate containing L-epi-2-inosose; a fourth stage comprising adding to said reaction solution filtrate a suitable reducing agent without effecting any isolation of L-epi-2-inosose from said reaction solution filtrate, and then effecting the reductive reaction of L-epi-2-inosose, thereby to produce epi-inositol and myo-inositol in said filtrate; a fifth stage comprising recovering from the resulting reaction solution of the reduction the so produced epi-inositol and myo-inositol; and a sixth stage comprising isolating epi-inositol from myo-inositol so recovered.

In the first stage of Procedure (D), the microorganism capable of converting myo-inositol into L-epi-2-inosose is cultivated under aerobic conditions in a liquid culture medium which is conventionally used, and the microbial cells of said microorganism are separated from the resulting culture broth. The microbial cells so separated are used in the second stage of Procedure (D). As said microbial cells, there may be used such microbial cells which were collected by the separation of the cells from the culture broth as obtained in the first step of the aforesaid Procedure (A). There may also be used such microbial cells which were obtained by cultivating the usable microorganism in a separate step under appropriate cultivation conditions. The separation and collection of the microbial cells may be effected by subjecting the culture broth in a known means to centrifugation, filtration, or other method.

In the second stage of Procedure (D), such an aqueous reaction medium composed of either an aqueous buffer solution or a liquid culture medium may be used as the liquid reaction medium in which the reaction of myo-inositol with the microbial cells is effected. As the liquid culture medium to be used here, there may be used any of those which are similar to that used in the first step of Procedure (A). As the buffer solution, there may be used a phosphate buffer solution, Good's CHES buffer solution and the like at a concentration of 10 to 500 mM, preferably 20 to 100 mM. The concentration of myo-inositol dissolved in said aqueous reaction medium is desirably in the range of 0.1 to 30% by weight. The conditions for the reaction of the microbial cells with myo-inositol may vary depending upon the nature of the microorganism to be used, the buffer solution or the liquid culture medium to be used. The reaction temperature is 5 to 60° C., preferably 10 to 45° C., and the reaction time is 1 to 50 hours, preferably 3 to 48 hours. The pH of the buffer solution or the liquid culture medium to be used as the aqueous reaction medium is in a range of pH 2 to 10, preferably pH 3 to 9. The reaction of the microbial cells with myo-inositol in the second stage gives the reaction solution containing L-epi-2-inosose.

In the third stage of Procedure (D), the microbial cells of the microorganism are separated from the reaction solution containing L-epi-2-inosose which has been obtained in the second stage of Procedure (D), with using a known method such as centrifugation, filtration and the like. Thereby, the reaction solution filtrate containing L-epi-2-inosose is obtained. In the subsequent fourth stage, the reductive reaction of L-epi-2-inosose is effected after a hydride has been added as the reducing agent to the reaction solution filtrate which is containing L-epi-2-inosose but is free from the microbial cells. So, epi-inositol and myo-inositol are produced. The reductive reaction in this fourth stage may be carried out in the same manner as explained for the third stage of Procedure (C).

Next, there is carried out the fifth stage of Procedure (D), wherein the epi-inositol and myo-inositol in the form of their aqueous solution are recovered from the resulting reaction solution of the above-mentioned reductive reaction which contained epi-inositol and myo-inositol. Then, there is effected the sixth stage wherein epi-inositol is recovered from said aqueous solution containing epi-inositol and myo-inositol. These fifth and sixth stages of procedure (D) may be carried out in the same manner as those disclosed for the fourth and fifth stages of Procedure (C) above.

The aforesaid Procedure (E) of the process of the second aspect of this invention is carried out in such a way that, before conducting the second stage of Procedure (C) or the fourth stage of Procedure (D) of the process of the second aspect of this invention, in which stage a reducing agent of an alkali metal hydride type is added to the above-mentioned culture broth supernatant or the reaction solution filtrate, followed by effecting the reduction of L-epi-2-inosose, there is conducted a preliminary step in which the pH of said culture broth supernatant or said reaction solution filtrate is once adjusted to a pH value of 8 to 11, preferably 9 to 10 by addition of sodium hydroxide or potassium hydroxide or sodium carbonate or potassium carbonate, and that the reductive reaction of L-epi-2-inosose is then effected with the addition of the reducing agent after said preliminary step. We have found from our another study that, when the pH of the reaction medium for said reductive reaction is once adjusted to an alkaline pH value as proposed above, the yield of epi-inositol as produced by the reductive reaction can increase by 1.3 to 1.5 times, while the yield of myo-inositol as by-produced can decrease by ½ to ¼ times, as compared with the case where the pH of the reaction medium for the reductive reaction has not been adjusted and where the reaction is effected in the reaction medium having a pH of 5 to 7 usually, so as to produce 6 to 7 parts of epi-inositol per 3 to 4 parts of myo-inositol by the reductive reaction of L-epi-2-inosose at the pH of 5 to 7. According to Procedure (E), the reduction of L-epi-2-inosose with the hydride agent in an aqueous reaction medium having a pH of 8 to 11 can produce epi-inositol in a very much higher yield than that of the by-produced myo-inositol.

The above-mentioned AB 10119 strain, AB 10215 strain and AB 10135 strain are novel microorganisms and each are useful for the production of L-epi-2-inosose from myo-inositol. According to a third aspect of this invention, therefore, there is provided, as a novel microorganism, Xanthomonas sp. AB 10119 strain which has a characteristic capability of converting myo-inositol into L-epi-2-inosose and has been deposited May 7, 1999 in a Japanese depository, the National Institute of Bioscience and Human Technology, Agency of Industrial Science and Technology, under a deposit number of FERM BP-7168.

According to a fourth aspect of this invention, there is provided, as a novel microorganism, Pseudomonas sp. AB 10215 strain which has a characteristic capability of converting myo-inositol into L-epi-2-inosose and has been deposited Mar. 31, 2000 in a Japanese depository, the National Institute of Bioscience and Human Technology, Agency of Industrial Science and Technology, under a deposit number of FERM BP-7170.

According to a fifth aspect of this invention, there is provided, as a novel microorganism, Erwinia sp. AB 10135 strain which has a characteristic capability of converting myo-inositol into L-epi-2-inosose and has been deposited Mar. 31, 2000 in a Japanese depository, the National Institute of Bioscience and Human Technology, Agency of Industrial Science and Technology, under a deposit number of FERM BP-7169.

According to the first and second aspects of this invention, L-epi-2-inosose of a high purity which is useful as starting material for the syntheses of medicines and agricultural chemicals, as well as epi-inositol which is useful as medicines can readily be produced, respectively, in an industrial scale and economically.

BEST EMBODIMENTS OF THE INVENTION

This invention is now further illustrated in detail with reference to the following Examples.

EXAMPLE 1

(a) First Example of Production of L-epi-2-inosose by Procedure (A) According to the First Aspect Process of this Invention (1) Production of L-epi-2-inosose (a First Experiment)
Into each of baffled Erlenmeyer flasks of 500 ml-capacity was poured a 100 ml-portion of a liquid culture medium (totally 3 liters) which contained 12.0% (360 g) of myo-inositol, 1.2% of yeast extract, 0.1% of $(NH_4)_2 SO_4$, 0.7% of $K_2 HPO_4$, 0.2% of $KH_2 PO_4$ and 0.01% of $MgSO_4\ 7H_2O$ and had the pH of 7. Then, the flasks containing the culture medium were sterilized in an autoclave. The sterilized culture medium in each flask was inoculated with Xanthomonas sp. AB 10119 strain (deposited under the deposit number of FERM BP-7168), and the inoculated bacterial strain was cultivated under shaking at 27° C. for 3 days. The resulting culture broth was centrifuged (8000 rpm. for 20 minutes) to afford the culture broth supernatant.

This culture broth supernatant was analyzed by a high performance liquid chromatography (HPLC) under the conditions of measurements shown below. As a result, it was confirmed that L-epi-2-inosose had been produced at a concentration of 66 mg/ml in said culture broth supernatant (at a conversion rate of L-epi-2-inosose from myo-inositol which was 55.6%). No myo-inositol was detected in said broth supernatant as obtained at this time.

The above mentioned conversion rate of L-epi-2-inosose from myo-inositol was calculated by the following calculation equation:

Conversion rate (%) of L-epi-2-inosose=[The number of moles of L-epi-2-inosose present in 1 ml of the broth supernatant:+The number of moles of myo-inositol initially present in 1 ml of the liquid culture medium]×100

The conditions of measurement for the high performance liquid chromatographic analysis are as follows:

Column: Wakosil $5NH_2$: 4.6×350 mm

Column temperature: 40° C.

Detector: RI DETECTOR ERC-7515A (ERMA CR. INC.)

Amount poured of the supernatant: 20 µl

Eluting Solvent: acetonitrile-water (4:1)

Time of elution for L-epi-2-inosose; 6.7 minutes.

(2) Production of L-epi-2-inosose (a Second Experiment)

Into each of 500 ml-capacity-baffled Erlenmeyer flasks was poured a 100 ml-portion of a liquid culture medium (totally 400 ml) which contained 25.0% (250 mg/ml) of myo-inositol, 1.0% of glucose and 0.7% of yeast extract, with the pH being not adjusted. Then, the flasks containing the culture medium were sterilized in an autoclave. The sterilized culture medium in each flask was inoculated with Xanthomonas sp. AB 10119 strain (deposited under the deposit number of FERM BP-7168), and the inoculated bacterial strain was cultivated under shaking at 27° C. for 5 days. The resulting culture broth was centrifuged (8000 rpm. for 20 minutes) to afford the culture broth supernatant.

This culture broth supernatant was analyzed by a high performance liquid chromatography (HPLC) under the conditions of measurement as shown above. As a result, it was confirmed that L-epi-2-inosose had been produced at a concentration of 247 mg/ml in said broth supernatant (at the conversion rate of 99.9%). No myo-inositol was detected in said broth supernatant as obtained at this time.

The above conversion rate of L-epi-2-inosose from myo-inositol was calculated by the calculation equation given in the above.

(3) Production of L-epi-2-inosose (a Third Experiment)

Into each of 500 ml-capacity-baffled Erlenmeyer flasks was poured a 100 ml-portion of a liquid culture medium which contained 4.0% (40 mg/ml) of myo-inositol, 0.2% of yeast extract, 0.1% of $(NH_4)_2 SO_4$, 0.7% of $K_2 HPO_4$, 0.2% of $KH_2 PO_4$ and 0.01% of $MgSO_4\ 7H_2O$ and had the pH of 7. Then, the flasks were sterilized in an autoclave. The sterilized culture medium in each flask was inoculated with Erwinia sp. AB 10135 strain (deposited under the deposit number of FERM BP-7169), and the inoculated bacterial strain was cultivated under shaking at 27° C. for 5 days. The resulting culture broth was centrifuged (8000 rpm. for 20 minutes) to afford the culture broth supernatant.

This culture broth supernatant was analyzed by a high performance liquid chromatography under the conditions of measurement as shown above. As a result, it was confirmed that L-epi-2-inosose had been produced at a concentration of 22 mg/ml in said broth supernatant (at the conversion rate of 55.6%). No myo-inositol was detected in said broth supernatant as obtained at this time.

The above conversion rate of L-epi-2-inosose from myo-inositol was calculated by the calculation equation given in the above.

(4) Production of L-epi-2-inosose (a Fourth Experiment)

Into each of 500 ml-capacity-baffled Erlenmeyer flasks was poured a 100 ml-portion of a liquid culture medium which contained 25.0% (250 mg/ml) of myo-inositol, 1.0% of glucose and 0.7% of yeast extract, with the pH being not adjusted. Then, the flasks were sterilized in an autoclave. The sterilized culture medium in each flask was inoculated with Pseudomonas sp. AB 10215 strain (deposited under the deposit number of FERM BP-7170), and the inoculated bacterial strain was cultivated under shaking at 27° C. for 5 days. The resulting culture broth was centrifuged (8000 rpm. for 20 minutes) to give the culture broth supernatant.

This culture broth supernatant was analyzed by a high performance liquid chromatography under the conditions of measurement shown above. As a result, it was confirmed that L-epi-2-inosose had been produced at a concentration of 244 mg/ml in said broth supernatant (at the conversion rate of 98.7%). No myo-inositol was detected in said broth supernatant as obtained at this time.

(b) Recovery and Isolation of L-epi-2-inosose

The culture broth supernatant as obtained in Example 1 (2) above was passed through a column (with an inner diameter of 2 cm×a height of 30 cm) which was packed with 80 ml of a strongly acidic cation-exchange resin, Duolite (Registered Trade Mark) C-20 ($H^+$ form). Then, this column was washed by passing 80 ml of an ion-exchanged water (that is, deionized water) therethrough. Then, the resultant effluent as obtained by the passage of the culture broth supernatant through said column was combined with the aqueous washings as obtained by washing said column with the deionized water. The resultant combined solution was passed through a column (with an inner diameter of 3 cm×a height of 30 cm) comprising 160 ml of a weakly basic anion-exchange resin, Duolite (Registered Trade Mark) 368S (in the free base form), followed by washing the column of the anion-exchange resin by passing 160 ml of deionized water therethrough.

The resultant effluent from the latter column and the resultant aqueous washings were combined together to afford an aqueous solution. This aqueous solution contained L-epi-2-inosose, but substantially did not contain any impurities.

This aqueous solution obtained as above was concentrated to a volume of 200 ml under a reduced pressure. To the concentrated solution was added a 3-folds-(by volume) of ethanol, and the resulting liquid mixture was allowed to stand overnight, thus yielding 60 g of colorless crystals of pure L-epi-2-inosose. The recovery rate of the purified product of L-epi-2-inosose was 60.7% at this time, and the overall recovery rate of L-epi-2-inosose was 60.6% on the basis of the starting myo-inositol.

The above-mentioned recovery rate of the purified product of L-epi-2-inosose was calculated according to the following calculation equation:

Recovery rate (%) of the purified product of L-epi-2-inosose=[The amount of the purified L-epi-2-inosose as isolated÷The amount of L-epi-2-inosose present in 400 ml of the culture broth supernatant before the purification]×100

The above-mentioned overall recovery rate of L-epi-2-inosose was calculated by the following calculation equation.

Overall recovery rate (%) of L-epi-2-inosose=[The number of moles of the purified L-epi-2-inosose as isolated÷The number of moles of myo-inositol initially present in 400 ml of the liquid culture medium]×100

EXAMPLE 2

Second Example of Production of L-epi-2-inosose by Procedure (A) According to the First Aspect Process of this Invention (1) Preparation of Seed Culture Into each of baffled Erlenmeyer flasks of 500 ml-capacity was poured a 100 ml-portion of a liquid culture medium which comprised 2.0% of myo-inositol, 0.2% of yeast extract, 0.1% of $(NH_4)_2 SO_4$, 0.7% of $K_2 HPO_4$, 0.2% of $KH_2 PO_4$ and 0.01% of $MgSO_4 \cdot 7H_2O$ and had the pH of 7. Then, the flasks were sterilized in an autoclave. The sterilized culture medium in each flask was inoculated with Xanthomonas sp. AB 10119 strain (FERM BP-7168), and the inoculated bacterial strain was cultivated under shaking at 27° C. for 1 day. The resulting culture broth was used as the seed culture for the following step of the process.

(2) Production of L-epi-2-inosose in 4 Liter-volume-jar Fermentors

Into each of 4 liter-capacity-jar fermentors was poured a 2.5 liter-portion of a liquid culture medium which comprised 12.0% of myo-inositol, 1.2% of yeast extract, 0.1% of $(NH_4)_2 SO_4$, 0.7% of $K_2 HPO_4$, 0.2% of $KH_2 PO_4$ and 0.01% of $MgSO_4 \cdot 7H_2O$ and had the pH of 7. Then, the jar fermentors were sterilized in an autoclave. The sterilized culture medium in each fermentor was inoculated with 25 ml of said seed culture of Xanthomonas sp. AB 10119 strain which was prepared in the stage (1) above. Then, the cultivation was carried out under aerobic conditions at a temperature of 27° C., at the rate of aeration of 1 vvm and at the number of agitator revolution of 200 rpm. The cultivation was carried out for 3 days during which the pH of the culture broth was automatically adjusted to pH 7±0.2 with addition of 5M NaOH aqueous solution and 3M hydrochloric acid. After the completed cultivation of 3 days, the resulting culture broth was centrifuged (8000 rpm, for 20 minutes), thereby to afford the culture broth supernatant as the resultant supernatant.

The culture broth supernatant as afforded was analyzed by a high performance liquid chromatography (HPLC) under such conditions of measurement which were similar to those as mentioned in the above. As a result, it was confirmed that L-epi-2-inosose was produced at a concentration of 60 mg/ml in the resultant culture broth supernatant (at the conversion rate of 50.6%).

The purification and isolation of L-epi-2-inosose from the above culture broth supernatant was carried out in the same manner as described in Example 1 (b). Thus, there was obtained 114 g of crystals (at a recovery rate of the purified L-epi-2-inosose of 76.0%). The overall recovery rate of the purified L-epi-2-inosose was 38.4% at this time on the basis of myo-inositol.

The above-mentioned conversion rate of L-epi-2-inosose was calculated in accordance with the calculation equation as given in Example 1 (b), and the above-mentioned recovery rate of the purified L-epi-2-inosose was calculated by the following calculation equation:

Recovery rate (%) of the purified L-epi-2-inosose=[The amount of the purified L-epi-2-inosose as isolated÷The amount of L-epi-2-inosose present in 2.5 liters of the culture broth supernatant before the purification]×100

The above-mentioned overall recovery rate of L-epi-2-inosose on the basis of myo-inositol was calculated by the following calculation equation:

Overall recovery rate (%) of L-epi-2-inosose=[The number of moles of the purified L-epi-2-inosose as isolated÷The number of moles of myo-inositol initially contained in 2.5 liters of the liquid culture medium]×100

EXAMPLE 3

Example of Production of L-epi-2-inosose by Procedure (B) of the First Aspect Process of this Invention (1) Production of Microbial Cells Into each of 500 ml-capacity-baffled Erlenmeyer flasks was poured a 100 ml-portion of a liquid culture medium (totally 2 liters) which comprised 0.5% of myo-inositol, 0.1% of $(NH_4)_2SO_4$, 0.7% of $K_2HPO_4$, 0.2% of $KH_2PO_4$ and 0.01% of $MgSO_4 \cdot 7H_2O$ and had the pH of 7. Then, the flasks were sterilized in an autoclave. The sterilized culture medium in each flask was inoculated with Xanthomonas sp. AB 10119 strain (FERM BP-7168), and the inoculated bacterial strain was cultivated under shaking at 27° C. for 3 days. The resulting culture broth was centrifuged to separate the microbial cells. The resulting microbial cells so separated were rinsed with 200 ml of 0.05 M phosphorate buffer solution (pH: 7.0) and then centrifuged again to give the rinsed microbial cells of the bacterium.

(2) Production of L-epi-2-inosose

The rinsed microbial cells as obtained (35 g) were added to 400 ml of 0.05 M phosphorate buffer solution (pH: 7.0) which contained 4 g of myo-inositol (at the concentration of myo-inositol of 10 mg/ml). The resulting mixture containing the added microbial cells was incubated at 30° C. for 24 hours under slow agitation by means of a stirrer. After the completion of the incubation, the resulting reaction solution containing the suspended microbial cells and the produced L-epi-2-inosose dissolved therein was analyzed by a liquid chromatography. It was shown that L-epi-2-inosose was produced and accumulated therein at the concentration of 6 mg/ml (at a conversion rate of 60.7%). The aforesaid reaction solution was centrifuged to separate the microbial cells and to afford the reaction solution filtrate. The isolation of L-epi-2-inosose from this reaction solution filtrate was carried out in the same manner as described in Example 1 (b) above, thereby to give 1.6 g of crystals of L-epi-2-inosose (at the recovery rate of the purified L-epi-2-inosose of 66.7%). The overall recovery rate of the purified L-epi-2-inosose was 40.4% on the basis of myo-inositol.

The above-mentioned conversion rate of L-epi-2-inosose was calculated similarly to Example 1 above, and the above-mentioned recovery rate of the purified L-epi-2-inosose was calculated by the following calculation equation:

Recovery rate (%) of the purified L-epi-2-inosose=[The amount of the purified L-epi-2-inosose as isolated÷The amount of L-epi-2-inosose initially contained in 400 ml of the reaction solution before the purification]×100.

The above-mentioned overall recovery rate of the purified L-epi-2-inosose on the basis of myo-inositol was evaluated by the following calculation equation:

Overall recovery rate (%) of the purified L-epi-2-inosose=[The number of moles of the purified L-epi-2-inosose as isolated/ The number of moles of myo-inositol as initially added to 400 ml of the phosphate buffer solution]×100

EXAMPLE 4

Example of Production of Epi-inositol by Procedure (C) of the Second Aspect Process of this Invention (1) Production of L-epi-2-inosose Into each of 500 ml-capacity-baffled Erlenmeyer flasks was poured a 100 ml-portion of a liquid culture medium (totally 2 liters) which comprised 25.0% (500 g) of myo-inositol, 1.0% of glucose and 2.5% of yeast extract, with the pH being not adjusted. Then, the flasks were sterilized in an autoclave. The sterilized culture medium in each flask was inoculated with Xanthomonas sp. AB 10119 strain (FERM BP-7168), and the inoculated bacterial strain was cultivated under shaking at 27° C. for 5 days. The resulting culture broth was centrifuged (8000 rpm., for 20 minutes) to afford the culture broth supernatant liquid.

This culture broth supernatant liquid was analyzed by a high performance liquid chromatography similarly to Example 1 (1). As a result, it was confirmed that 415 g of L-epi-2-inosose was produced in said culture broth supernatant liquid (at the conversion rate of L-epi-2-inosose of 83.9% from myo-inositol).

(2) Production of Epi-inositol

To 2 liters of the culture broth supernatant liquid containing L-epi-2-inosose which resulted from the above stage (1), was added slowly 29.2 g of sodium boron hydride as a reducing agent. The reductive reaction of L-epi-2-inosose was then effected at room temperature. After the completion of the reductive reaction, the broth supernatant liquid (namely, the reaction solution resulted from the reductive reaction) was analized by a high performance liquid chromatography under the conditions of measurement as given below. As a result, it was confirmed that the reaction solution resulted from the reductive reaction (namely, the broth supernatant liquid as afforded after the reductive reaction) had contained 235.8 g of the produced epi-inositol and 102.4 g of the by-produced myo-inositol (at the overall reaction yield of epi-inositol plus myo-inositol which was of 80.6%). The conversion rate of epi-inositol from L-epi-2-inosose was 56.2%. The measurement conditions for the above-mentioned high performance liquid chromatography are as follows.

Column: Wakosil 5NH$_2$: 4.6×250 mm

Column temperature: 40° C.

Detector: RI DETECTER ERC-7515A (ERMA CR. INC.)

Amount of the reaction solution poured: 20 µl

Elution Solvent; acetonitrile-water (4:1)

Elution time for epi-inositol: 8.5 minutes

The above-mentioned overall recovery rate (%) of epi-inositol plus myo-inositol was evaluated by the following calculation equation:

Overall recovery rate (%)=[(The sum total of the number of moles of epi-inositol plus the number of moles of myo-inositol present in the broth supernatant as afforded after the reductive reaction)÷(The number of moles of L-epi-2-inosose firstly present in the broth supernatant as provided before the reductive reaction)]×100

The above-mentioned conversion rate of epi-inositol from L-epi-2-inosose was evaluated given by the following calculation equation:

The conversion rate (%) of epi-inositol=[The number of moles of epi-inositol present in the broth supernatant liquid as afforded after the reductive reaction÷The number of moles of L-epi-2-inosose present in the broth supernatant liquid as provided before the reductive reaction]×100

(3) First Experiment of the Recovery and Isolation of Epi-inositol

The reaction solution (namely, the broth supernatant liquid as afforded after the reductive reaction) obtained in the above stage (2) was divided into two halves. One half portion of said reaction solution was passed through a column (with an inner diameter of 5 cm×a height of 30 cm) comprising 300 ml of a strongly acidic cation-exchange resin, Duolite (Registered Trade Mark) C-20 (H$^+$ form), to give the effluent from the column. Then, the column was washed by passing 400 ml of deionized water therethrough. The resultant effluent and the resultant aqueous washings were combined together, and the so combined solution was passed through a column (with an inner diameter of 5 cm×a height of 60 cm) comprising 600 ml of a strongly basic anion-exchange resin, Duolite (Registered Trade Mark) A-113 (OH$^-$ form), to give the effluent. Then, this column was washed by passing 700 ml of deionized water therethrough.

The resulting effluent from the column and the resulting aqueous washings were combined together. The resulting aqueous solution so combined did contain the produced epi-inositol and the by-produced myo-inositol, but substantially did not contain the impurities.

This aqueous solution so combined and obtained as above was concentrated to a volume of 300 ml under a reduced pressure. A one-fourth portion (75 ml) of the resultant concentrated solution (300 ml) was passed through a column (with an inner diameter of 5 cm×a height of 200 cm) comprising 1500 ml of a strongly basic anion-exchange resin, Amberlite (Registered Trade Mark) CG-400 (OH$^-$ form), and then this column was eluted by passing a volume of deionized water therethrough. The resulting eluate from this column was collected separately in fractions containing mainly myo-inositol, and in fractions containing mainly the desired epi-inositol. The remaining three fourth portions (225 ml) of the said concentrated solution were subjected to similar treatments with columns of Amberlite CG-400 (OH$^-$ form) in such a way that there could be obtained eluate fractions containing epi-inositol alone therein. These eluate fractions as obtained were concentrated to dryness to give 73 g of epi-inositol. Further, this epi-inositol was dissolved in water to give a 15% aqueous solution, to which was then added a twice volume of ethanol. The resulting liquid mixture was allowed to stand overnight for recrystallization of epi-inositol. Thus, there was given 63 g of crystals of pure epi-inositol (at the recovery rate of the purified epi-inositol of 53.4%). The overall yield of epi-inositol from myo-inositol was 25.2%.

The above-mentioned recovery rate of epi-inositol was evaluated by the following calculation equation:

The recovery rate (%) of the purified epi-inositol=[The amount of the crystalline epi-inositol as isolated/The amount of epi-inositol present in the broth supernatant liquid as afforded after the reductive reaction]×100

The above-mentioned overall recovery rate of epi-inositol from myo-inositol was calculated by the following calculation equation:

The overall recovery rate (%) of epi-inositol=[The amount of the crystalline epi-inositol as isolated/The amount of myo-inositol initially present in 1 liter of the liquid culture medium]×100

(4) Second Experiment of the Recovery and Isolation of Epi-inositol

The other half portion of the reaction solution (the broth supernatant liquid as afforded after the reductive reaction) as previously divided in the above stage (3) was passed through a column (with an inner diameter of 5 cm×a height of 30 cm) comprising 300 ml of a strongly acidic cation-exchange resin, Duolite (Registered Trade Mark) C-20 (H⁺ form), to give the effluent from said column. Then, this column was washed by passing 400 ml of deionized water therethrough. The resultant effluent liquid and the resultant aqueous washings were combined together and then passed through a column (with an inner diameter of 5 cm of×a height of 60 cm) comprising 600 ml of a strongly basic anion-exchange resin, Duolite (Registered Trade Mark) A-113 (OH⁻ form), to give the effluent. And then, this column was washed by passing 700 ml of deionized water therethrough.

The resultant effluent from the latter column and the resultant aqueous washings were combined together, too. The aqueous solution thus obtained was concentrated to a volume of 300 ml under a reduced pressure. The resulting concentrated solution (300 ml) was passed through a column (with an inner diameter of 5 cm×a height of 200 cm) comprising 1500 ml of a strongly acidic cation-exchange resin, Diaion (Registered Trade Mark) UBK 520M (Ca⁺ form), to give the effluent. This column was then eluted by passing a volume of deionized water therethrough. The resulting eluate from this column was collected separately in fractions containing mainly myo-inositol, and also in fractions containing mainly the desired epi-inositol. From this chromatographic process, there was obtained 75 g of epi-inositol. Further, this epi-inositol was dissolved in water to give a 15% aqueous solution, to which was then added a twice volume of ethanol. The resulting mixture was allowed to stand overnight for the recrystallization purpose. Thus, there was given 66 g of crystals of pure epi-inositol (a the recovery rate of the purified epi-inositol of 56.0%). The overall yield of the purified epi-inositol on the basis of the myo-inositol used as the starting material was 26.4%.

The recovery rate of the purified epi-inositol and the overall recovery rate of the same were calculated in the same way as in the above stage (3).

EXAMPLE 5

Example of Production of Epi-inositol by Procedures (C) and (E) of the Second Aspect Process of this Invention (1) Production of L-epi-2-inosose Into each of 500 ml-capacity-baffled Erlenmeyer flasks was poured a 100 ml-portion of a liquid culture medium which comprised 25.0% of myo-inositol, 1.0% of glucose and 0.7% of yeast extract, with the pH being not adjusted. Then, the flasks were sterilized in an autoclave. The sterilized culture medium in each flask was inoculated with Xanthomonas sp. AB 10119 strain (FERM BP-7168), and the inoculated bacterial strain was cultivated under shaking at 27° C. for 5 days. The resulting culture broth was centrifuged (8000 rpm. for 20 minutes) to afford the culture broth supernatant.

This broth supernatant liquid was analyzed by a high performance liquid chromatography in the same manner as in Example 1 (1). As a result, it was confirmed that 23 g of L-epi-2-inosose was produced in said broth supernatant liquid (at the conversion rate of L-epi-2-inosose of 93.0% on the basis of myo-inositol).

(2) Production of Epi-inositol

To 100 ml of said broth supernatant liquid containing the L-epi-2-inosose, which had been afforded from the stage (1) above, was added 5 M aqueous sodium hydroxide solution to adjust the pH of the supernatant liquid to pH10. Immediately after this, there was added to the supernatant liquid of pH 10, slowly 1.3 g of sodium boron hydride. The reductive reaction was then effected at room temperature. After the completion of the reaction, the broth supernatant liquid as reacted (namely, the reaction solution resulted from the reductive reaction) was analyzed by a high performance liquid chromatography under the conditions of measurement as described in Example 4 (2). As a result, it was confirmed that said reaction solution from the reductive reaction (namely, the broth supernatant liquid as reacted) did contain 18.4 g of the produced epi-inositol and 0.8 g of the by-produced myo-inositol (at the overall reaction yield of epi-inositol plus myo-inositol of 82.6%). The conversion rate of epi-inositol from L-epi-2-inosose was 79.1%.

The above-mentioned overall reaction yield (%) of epi-inosirol plus myo-inositol was evaluated by the following calculation equation:

The overall reaction yield of epi-inositol plus myo-inositol=[The sum total of the number of moles of epi-inositol and the number of moles of myo-inositol both present in the broth supernatant liquid as afforded after the reductive reaction÷

The number of moles of L-epi-2-inosose firstly present in the broth supernatant liquid as provided before the reductive reaction]×100

The above-mentioned conversion rate of epi-inositol from L-epi-2-inosose was evaluated by the following calculation equation:

The conversion rate (%) of epi-inositol from L-epi-2-inosose=[The number of moles of epi-inositol present in the broth supernatant liquid as afforded after the reductive reaction÷The number of moles of L-epi-2-inosose present in the broth supernatant liquid as provided before the reductive reaction]×100

(3) Recovery and Isolation of Epi-inositol

The recovery, purification and isolation of epi-inositol from said reaction solution coming from the reduction reaction were effected in the same manner as described in Example 4 (4). Epi-Inositol was obtained as crystals at a yield of 15.7 g. The recovery rate of the purified epi-inositol from the epi-inositol which was present initially in the reaction solution, was 85.3% at this time. The yield of epi-inositol based on the L-epi-2-inosose which was firstly present in the reaction solution prior to the reduction, was 67.5%. The overall recovery rate of the purified epi-inositol on the basis of myo-inositol used as the starting material was 62.8%.

The above-mentioned recovery rate of the purified epi-inositol on the basis of the epi-inositol firstly present in the reaction solution after the reductive reaction was evaluated by the following calculation equation:

The recovery rate (%) of the purified epi-inositol=[The amount of the purified epi-nositol as isolated÷The amount of epi-inositol firstly present in 100 ml of the reaction solution, namely the broth supernatant liquid as afforded after the reductive reaction]×100

The above-mentioned yield of the purified epi-inositol based on L-epi-2-inosose was evaluated by the following calculation equation:

Yield (%) of the purified epi-inositol=[The number of moles of the purified epi-inositol as isolated÷The number of moles of L-epi-2-inosose present in 100 ml of the broth supernatant liquid as provided before the reductive reactive]×100

The above-mentioned overall recovery rate of the purified epi-inositol from myo-inositol was calculated by the following calculation equation:

The overall recovery rate (%) of the purified epi-inositol=[The amount of the purified epi-inositol as isolated÷The amount of myo-inositol initially present in 100 ml of the liquid culture medium at the start of the cultivation]×100

Industrial Applicability

According to this invention, it is feasible to produce from myo-inositol in a facile and efficient way, L-epi-2-inosose which is useful as an intermediate for the syntheses of medicines. According to this invention, further, it is feasible to produce readily and efficiently by the reduction of L-epi-2-inosose, epi-inositol which is useful as a variety of medicines. Thus, the processes according to this invention are useful for industrial purposes.

What is claimed is:

1. A process for the production of L-epi-2-inosose, characterized in that the process comprises cultivating a microorganism selected from the group consisting of Xanthomonas sp. AB 10119 strain (deposited under FERM BP-7168), Pseudomonas sp. AB 10215 strain (deposited under FERM BP-7170) and Erwinia sp. 10135 strain (deposited under FERM BP-7169), under aerobic conditions in a liquid culture medium containing an amount of myo-inositol, carbon sources and nitrogen sources, whereby myo-inositol is contacted and reacted with the cells of said microorganism in the culture medium to produce and accumulate L-epi-2-inosose in the resulting culture broth.

2. The process as claimed in claim 1, wherein the culture broth or the reaction solution containing the microbial cells and L-epi-2-inosose as produced and accumulated therein is obtained in the process of claim 1, followed by removing the microbial cells of the microorganism from said culture broth or said reaction solution, and wherein the resulting culture broth supernatant or the resulting filtrate of the reaction solution as obtained upon the removal of the microbial cells from said culture broth or from said reaction solution containing L-epi-2-inosose therein is then subjected to a treatment with ion-exchange resin(s) or to a treatment with activated carbon or to a treatment for crystallization of L-epi-2-inosose or to any combination of these treatments, whereby L-epi-2-inosose of a high purity is recovered from said culture broth supernatant or from said filtrate of the reaction solution.

3. A process for the production of L-epi-inosose, which comprises the steps of cultivating a microorganism selected from the group consisting of Xanthomonas sp. AB 10119 strain (deposited under FERM BP-7168), Pseudomonas, sp. AB 10215 strain (deposited under FERM BP-7170) and Erwinia sp. 10135 strain (deposited under FERM BP-7169), under aerobic conditions in a liquid culture medium, separating the microbial cells of the cultivated microorganism from the resulting culture broth, adding the so separated microbial cells to an aqueous buffer solution or a liquid culture medium containing an amount of myo-inositol dissolved therein, and contacting and reacting the so added microbial cells with myo-inositol in said aqueous buffer solution or said liquid culture medium to convert myo-inositol and to produce L-epi-2-inosose in the resulting reaction solution or the resulting culture broth.

4. A process for the production of epi-inositol, characterized in that the process comprises the steps of contacting and reacting the cells of a microorganism selected from the group consisting of Xanthomonas sp. AB 10119 strain (deposited under FERM BP-7168), Pseudomonas sp. AB 10215 strain (deposited under FERM BP-7170) and Erwinia sp. 10135 strain (deposited under FERM BP-7169), with myo-inositol in an aqueous reaction medium to produce L-epi-2-inosose in said aqueous reaction medium, thereby affording the resulting reaction solution containing the microbial cells of said microorganism and the produced L-epi-2-inosose therein, removing the microbial cells from said reaction solution to give a reaction solution filtrate containing L-epi-2-inosose, adding an appropriate reducing agent directly to said reaction solution filtrate containing L-epi-2-inosose, and reacting the reducing agent with L-epi-2-inosose to produce epi-inositol and myo-inositol.

5. The process as claimed in claim 4, which comprises the step of cultivating under aerobic conditions a microorganism selected from the group consisting of Xanthomonas sp. AB 10119 strain (deposited under FERM BP-7168), Pseudomonas sp. AB 10215 strain (deposited under FERM BP-7170) and Erwinia sp. 10135 strain (deposited under FERM BP-7169), in an aqueous reaction medium composed of a liquid culture medium containing an amount of myo-inositol, carbon sources and nitrogen sources, thereby to contact and react myo-inositol with the cells of said microorganism in said aqueous reaction medium, and thereby producing and accumulating L-epi-2-inosose in the resulting culture broth to afford a culture broth which is the resulting reaction solution containing the microbial cells of said microorganism and L-epi-2-inosose therein; as well as the step of removing the microbial cells of said microorganism from said resulting reaction solution, to produce a culture broth supernatant which is the filtrate of said reaction solution containing L-epi-2-inosose; and the steps of then adding directly to said culture broth supernatant an alkali metal boron hydride, an alkali metal tri-alkoxyboron hydride or an alkali metal boron cyanide as the reducing agent, and effecting the reductive reaction of L-epi-2-inosose with this reducing agent, thereby to produce epi-inositol and myo-inositol in said culture broth supernatant, the step of recovering the epi-inositol and myo-inositol from the resultant reaction solution of the reductive reaction, and the step of separating the recovered epi-inositol and myo-inositol from each other.

6. The process as claimed in claim 5, wherein, before conducting the step of effecting the reductive reaction of L-epi-2-inosose with the reducing agent as added, there is interposed a preliminary step in which the pH of the aqueous medium composed of the culture broth supernatant or of the reaction solution filtrate containing L-epi-2-inosose therein is once adjusted to an alkaline pH in a range of pH 8 to 12; and wherein there is then conducted the step which comprises adding to said aqueous medium containing L-epi-2-inosose and having a pH of 8 to 12 an alkali metal boron hydride, an alkali metal tri-alkoxyboron hydride or an alkali metal boron cyanide as the reducing agent, and effecting the reductive reaction of L-epi-2-inosose with said reducing agent, whereby the desired epi-inositol is produced in a yield much greater than that of the by-produced myo-inositol.

7. The process as claimed in claim 4, which comprises the steps of cultivating under aerobic conditions a microorganism selected from the group consisting of Xanthomonas sp. AB 10119 strain (deposited under FERM BP-7168), Pseudomonas sp. AB 10215 strain (deposited under FERM BP-7170) and Erwinia sp. 10135 strain (deposited under FERM BP-7169), in a liquid culture medium containing carbon sources and nitrogen sources, thereby to afford a culture broth of said microorganism, and then separating the microbial cells of said microorganism from the resultant culture broth; the step of contacting and reacting the so separated microbial cells of said microorganism with myo-inositol in an aqueous reaction medium composed of an aqueous buffer solution or of a liquid culture medium, to produce L-epi-2-inosose in said aqueous reaction medium; the step of removing the microbial cells of said microorganism from the resulting aqueous reaction solution containing the microbial cells and the so produced L-epi-2-inosose therein, to afford a filtrate of said reaction solution from which the microbial cells have been removed but in which L-epi-2-inosose remains dissolved; the steps of adding to said reaction solution filtrate an alkali metal boron hydride, an alkali metal tri-alkoxyboron hydride or an alkali metal boron cyanide as a reducing agent, and effecting the reductive reaction of L-epi-2-inosose with said reducing agent, thereby to produce epi-inositol and myo-inositol in said reaction solution filtrate; the step of recovering the epi-inositol and myo-inositol from the resulting reaction solution of the reductive reaction which is containing the epi-inositol and myo-inositol so produced; and the step of separating the so recovered epi-inositol and myo-inositol from each other.

8. The process as claimed in claim 7, wherein, before conducting the step of effecting the reductive reaction of L-epi-2-inosose with the reducing agent as added, there is interposed a preliminary step in which the pH of the aqueous medium composed of the culture broth supernatant or of the reaction solution filtrate containing L-epi-2-inosose therein is once adjusted to an alkaline pH in a range of pH 8 to 12; and wherein there is then conducted the step which comprises adding to said aqueous medium containing L-epi-2-inosose and having a pH of 8 to 12 an alkali metal boron hydride, an alkali metal tri-alkoxyboron hydride or an alkali metal boron cyanide as the reducing agent, and effecting the reductive reaction of L-epi-2-inosose with said reducing agent, whereby the desired epi-inositol is produced in a yield much greater than that of the by-produced myo-inositol.

9. The process as claimed in claim 4, wherein the reducing agent to be used for the reductive reaction of L-epi-2-inosose is chosen from sodium boron hydride, lithium boron hydride, potassium boron hydride, sodium tri-methoxyboron hydride and sodium boron cyanide hydride.

10. The process as claimed in claim 4, wherein the aqueous reaction medium to be used is water, and the reducing agent to be used is sodium boron hydride.

11. A biologically pure culture of Xanthomonas sp. AB 10119 strain which has a characteristic nature capable of converting myo-inositol into L-epi-2-inosose and which has been deposited under the deposit number of FERM BP-7168 in the National Institute of Bioscience and Human Technology, Agency of Industrial Science and Technology, in Japan.

* * * * *

UNITED STATES PATENT AND TRADEMARK OFFICE
CERTIFICATE OF CORRECTION

PATENT NO. : 6,818,430 B1
DATED : November 16, 2004
INVENTOR(S) : Takahashi et al.

It is certified that error appears in the above-identified patent and that said Letters Patent is hereby corrected as shown below:

<u>Title page,</u>
Item [22], PCT Filed, should read as follows:
-- Jun. 7, 2000 --

Signed and Sealed this

First Day of February, 2005

JON W. DUDAS
*Director of the United States Patent and Trademark Office*